(12) United States Patent
Heinlein et al.

(10) Patent No.: US 7,916,914 B2
(45) Date of Patent: Mar. 29, 2011

(54) METHOD FOR PROCESSING FINDINGS ENTERED IN A MAMMOGRAM

(75) Inventors: Peter Heinlein, München (DE); Marco Blumenthal, Jena (DE); Anca Dima, München (DE)

(73) Assignee: Image Diagnost International GmbH, Muchen (DE)

( * ) Notice: Subject to any disclaimer, the term of this patent is extended or adjusted under 35 U.S.C. 154(b) by 0 days.

(21) Appl. No.: 12/494,389

(22) Filed: Jun. 30, 2009

(65) Prior Publication Data

US 2010/0027859 A1 Feb. 4, 2010

(30) Foreign Application Priority Data

Jul. 30, 2008 (DE) .......................... 10 2008 035 566

(51) Int. Cl.
*G06K 9/00* (2006.01)
(52) U.S. Cl. ........................ 382/128; 382/131; 382/132
(58) Field of Classification Search .................. 382/100, 382/128, 131, 132
See application file for complete search history.

(56) References Cited

U.S. PATENT DOCUMENTS

| | | | |
|---|---|---|---|
| 6,757,415 B1 * | 6/2004 | Rogers et al. ................. | 382/130 |
| 6,801,645 B1 * | 10/2004 | Collins et al. ................. | 382/130 |
| 6,813,375 B2 * | 11/2004 | Armato, III et al. .......... | 382/131 |
| 2008/0292194 A1 * | 11/2008 | Schmidt et al. ............... | 382/217 |
| 2009/0220139 A1 * | 9/2009 | Schneider et al. ............ | 382/132 |

* cited by examiner

*Primary Examiner* — Bhavesh M Mehta
*Assistant Examiner* — Stephen R Koziol
(74) *Attorney, Agent, or Firm* — Global Patent Operation; Jonathan E. Thomas

(57) ABSTRACT

A method for processing findings entered in a mammogram. A digital mammogram is displayed via an evaluation device. Via an input device the findings are entered directly into the displayed mammogram and are automatically transferred from the mammogram into a findings input mask. To transfer the findings from the mammogram into the findings input mask, a contour line of an object area surrounding an object of the mammogram is determined. An object area of the mammogram is divided into two partial areas. Each partial area is imaged onto an allocated mask region of the findings input mask. The entered findings are allocated to one of the partial areas and are transferred into the findings input mask with reference to the allocated partial area. In this manner, a location of findings entered in a mammogram relative to the nipple can reliably be determined and transferred into a findings input mask.

9 Claims, 5 Drawing Sheets

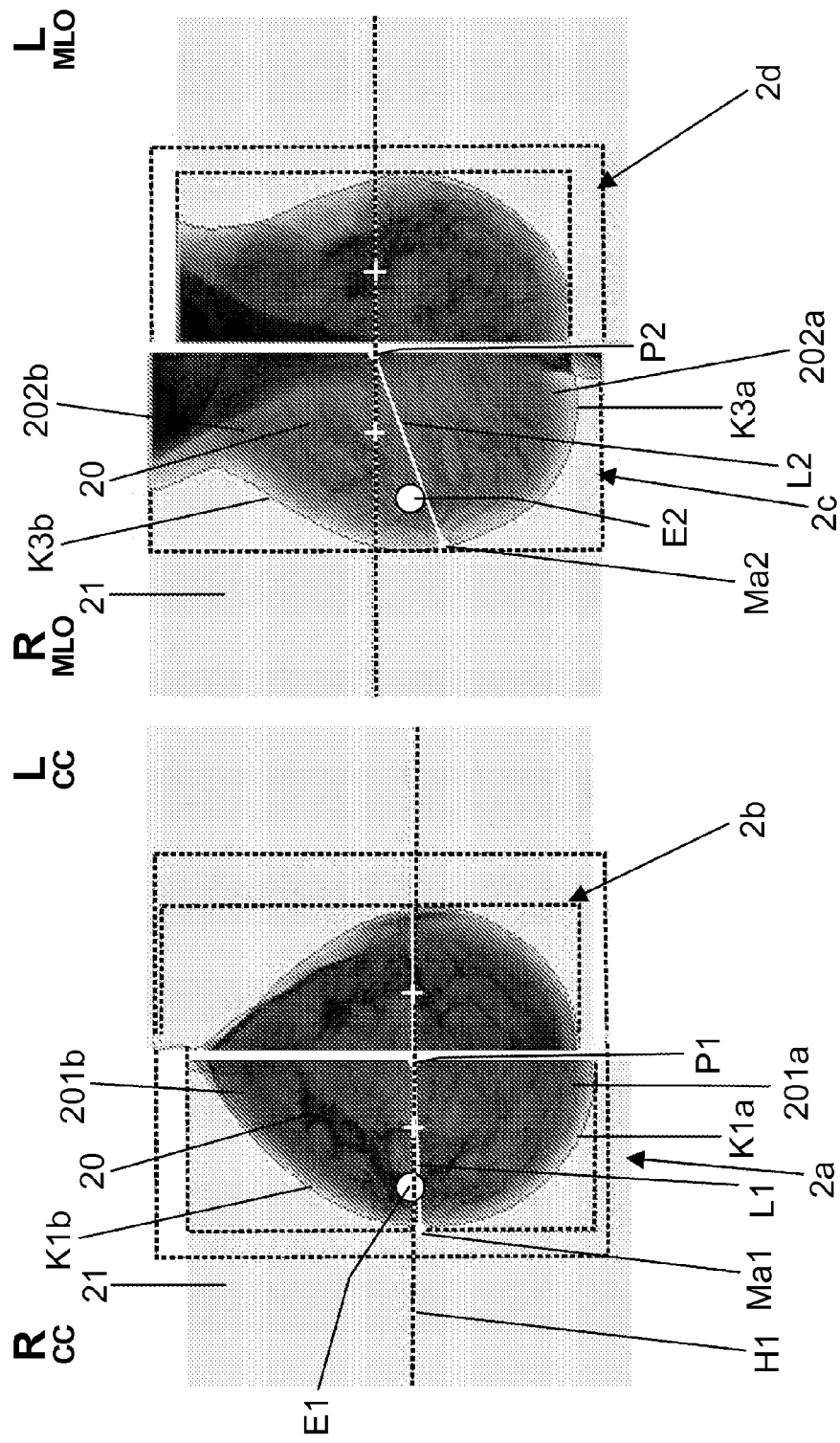

METHOD FOR PROCESSING FINDINGS ENTERED IN A MAMMOGRAM

CROSS-REFERENCE TO RELATED APPLICATIONS

This application claims priority under 35 U.S.C. §119(a)-(d) or (f) to prior-filed, co-pending GERMAN patent application serial number 2008035566.6, filed on Jul. 30, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The field of the invention relates to mammography generally, and more particularly to a method for processing findings entered in a mammogram.

2. Description of Related Art

In such a method for processing findings entered in a mammogram, as it is known for instance from DE 10 2006 021 037 A1, a digital mammogram is displayed via an evaluation device, the findings are directly entered into the mammogram displayed via the evaluation device using an input device, and the findings are automatically transferred from the mammogram into a findings input mask, which can for instance be displayed on a separate screen. For transferring the findings from the mammogram into the findings input mask, the contour line of an object area surrounding an object of the mammogram is determined and the findings are transferred into the input mask with reference to the contour line.

For displaying a mammogram, an evaluation device, for instance in the form of a workstation, conventionally employ an image viewer, in particular a PACS viewer (PACS: Picture Archiving and Communication System) and a findings input window (RIS-Client, RIS: Radiology Information System). In conventional evaluation devices, the physician views the mammogram in the image viewer and subsequently must switch to the findings input window, wherein findings input can be performed by manual text input, dictation with recording or speech recognition, but always is effected in the separate input window.

Regular mammography screening in particular involves the problem that a physician must evaluate a great number of mammograms in a short time. In conventional evaluation devices it is disadvantageous that the physician is distracted from the image when entering the findings, since the findings input must be performed in the separate findings input window, the effective time to be used by the physician for the visual viewing and diagnosis of the mammogram is reduced thereby, and switching between findings input and viewing leads to an increased susceptibility to faults in diagnosis.

Furthermore, transmission errors can occur, frequently due to the fact that as an essential information during findings input the physician must document the location of the findings in the mammogram and indicate the same by suitable, but frequently inaccurate location indications in the separate findings input window.

As compared to such conventional evaluation devices, DE 10 2006 021 037 A1 provides a method, in which the findings can directly be entered in the mammogram and the findings then are transferred automatically from the mammogram into a standardized findings input mask. This is effected in that a contour line determined from the mammogram is compared with a standardized contour of the findings input mask, and the coordinates of the findings together with further information entered are transferred into the findings input mask and converted into a clock time model. In the clock time model, the findings are indicated in the manner of a clock time, wherein the clock time model corresponds to a front view of a breast with the nipple as center, and the findings are stored with an indication of direction with reference to the nipple. One problem, however, which arises here, consists in the fact that the clock time model is discontinuous for findings in the region of the nipple: depending on whether the findings are located just above or below or to the right or left of the nipple, the location indication of the findings in the clock time model will jump from the "top" to the "bottom" or from the "right" to the "left" and vice versa. For transferring the findings from the mammogram into the findings input mask, the location of the findings relative to the nipple—e.g. the information as to whether the findings are above or below the nipple—therefore must reliably be determined and be transferred correctly.

BRIEF SUMMARY OF THE INVENTION

Embodiments of the invention may provide a method by means of which the location of findings entered in a mammogram relative to the nipple can reliably be determined and be transferred into a findings input mask.

In a method as mentioned above, it is provided in accordance with one embodiment of the invention that the object area of the mammogram is divided into two partial areas, which each are imaged onto an allocated mask region of the findings input mask, wherein the findings entered are allocated to one of the partial areas and transferred into the findings input mask with reference to the allocated partial area.

The method in accordance with one embodiment of the invention proceeds from the basic idea to treat a breast imaged in a mammogram for processing findings directly entered in the mammogram not as one uniform object, but to model the same as two objects which are continuously connected with each other. For this purpose, the object area of the mammogram which contains the breast is divided into two partial areas which are continuously connected with each other and are imaged on two mask regions of the findings input mask for transferring the findings entered in the mammogram into the findings input mask. The findings entered here are unambiguously allocated to one of the partial areas. This allocation is maintained, so that even after transferring the findings into the findings input mask, the findings entered are allocated to the corresponding mask region in the findings input mask and thus are unambiguously localized in the findings input mask with reference to the nipple.

Treating the object area of a mammogram as two partial areas has the advantage that discontinuities are avoided when transferring findings entered in the mammogram into a findings input mask. Because the unambiguous allocation of the findings to one partial area, it is excluded in particular that findings located in a mammogram approximately at the level of the nipple erroneously are stored for instance as "located above the nipple", although the findings actually are located just below the nipple. This is essential, as in the transformation and storage of the findings into a clock time model with reference to the nipple, the information "above/below" or "to the right/left" of the nipple determines whether the findings are located in the upper or lower half or in the right or left half of the clock time model. A mislocation can, for instance, lead to the fact that instead of the clock time "12 o'clock" the diametrically opposite clock time "6 o'clock" is stored. Due to an embodiment of the method of the invention and the unambiguous allocation of the findings to a partial area of the breast, this mislocation is excluded.

Advantageously, the object area is divided into the partial areas using a nipple line which extends through the nipple of a breast represented in the mammogram. The nipple line can extend through the nipple and a starting point of an altitude line extending horizontally through the image center of gravity of the mammogram. The position of the nipple is determined automatically, without an interaction of a user being necessary for this purpose.

The nipple line can be displayed during input of the findings, so that the user—for instance a physician reading the mammogram—can see already when entering the findings whether the findings are located above or below the nipple line, and can check whether the findings are correctly transferred into the findings input mask.

Advantageously, the nipple line can also be adjustable interactively, so that the nipple line possibly can subsequently be corrected in the case of an inaccurate determination of the location of the nipple. The coordinates of the findings in the findings input mask are corrected automatically in dependence on the adjusted nipple line, so that the correct coordinates of the findings are represented in the findings input mask at any time.

The nipple line divides the breast represented in the mammogram into an upper and a lower partial area. Depending on whether the findings entered are located above or below the nipple line, the findings are allocated either to the upper partial area or to the lower partial area. When imaging the two partial areas of the breast onto the corresponding mask regions of the findings input mask, this allocation is maintained, so that it is ensured that findings located for instance below the nipple line also are represented in the findings input mask as being located below the nipple line.

The breast included in the object area, which is shown in the mammogram, is separated from a background region of the mammogram by a contour line. For processing the mammogram, this contour line is detected in advance and forms the basis for the further processing of the mammogram. The partial areas of the object area each are defined section by section by a partial contour, which corresponds to a section of the contour line. When imaging the partial areas of the object area of the mammogram onto the corresponding mask regions of the findings input mask, the partial contours of the partial areas of the object area of the mammogram each are imaged onto a partial contour of the mask regions of the findings input mask, wherein the nipple line, i.e. the line connecting the partial areas with each other, is imaged continuously and thus, the partial areas imaged onto the findings input mask remain continuously connected with each other. The partial areas defined section by section by the nipple line and the respective partial contour thus each are separately imaged onto the findings input mask, with the connecting nipple line being maintained continuously.

Imaging the partial areas of the object area of the mammogram can for instance be effected using a square or linear deformation. Due to the square or linear deformation, each partial area is imaged onto the corresponding mask region of the findings input mask, wherein imaging is effected separately for each partial area of the object area, but the connection of the partial areas remains continuous.

After transferring the findings into the findings input mask by imaging the partial areas, the coordinates of the findings advantageously are transformed into a clock time model and output and stored with reference to the clock time model. By imaging the partial areas, the allocation of the findings entered is unambiguous, so that the location relative to the nipple is defined unambiguously and is correctly transferred into the findings input mask.

BRIEF DESCRIPTION OF THE DRAWINGS

The ideas underlying embodiments of the invention will subsequently be explained in detail with reference to the embodiments illustrated in the Figures, in which:

FIG. 4 shows mammograms with findings entered;

DETAILED DESCRIPTION OF THE INVENTION

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

Figure 1:
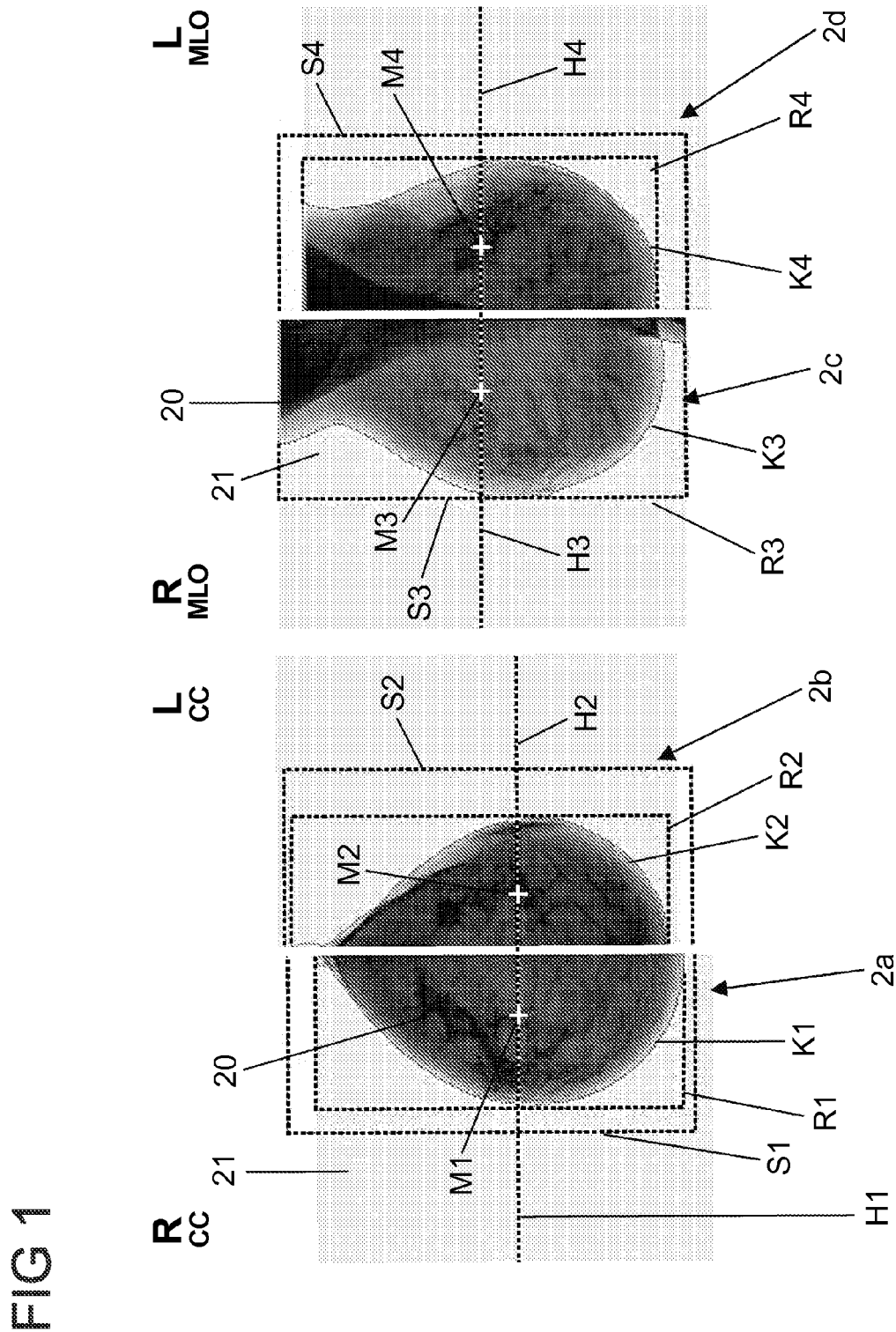
FIG. 1 shows mammograms of a right and a left breast displayed on an evaluation device in a mediolateral-oblique (MLO) and a cranio-caudal (CC) view.

FIG. 1 shows views of four digitally present mammograms 2a, 2b, 2c, 2d, which are displayed on an evaluation device. The digital mammograms 2a, 2b, 2c, 2d represent different views of a breast imaged in an object area 20 against a background region 21, namely mediolateral-oblique (MLO) mammograms 2c, 2d and cranio-caudal mammograms 2a, 2b of a left (L) and a right (R) breast. The mammograms 2a, 2b, 2c, 2d can have been generated using a direct-digital X-ray apparatus or digitized subsequently, when using an analogue X-ray apparatus.

The evaluation device in particular can constitute a workstation, which receives a mammogram 2a, 2b, 2c, 2d to be processed from an X-ray apparatus, which processes the mammogram 2 and outputs and represents the same via an output unit, for instance a monitor.

In connection with mammography examinations, mammograms 2a, 2b, 2c, 2d of the left and the right breast of a patient are recorded and evaluated by a physician. In a mammography examination, four mammograms 2a, 2b, 2c, 2d regularly are made, wherein one cranio-caudal (CC) and one mediolateral-oblique (MLO) picture each is made of each breast of a patient. The pictures thus obtained each are compared with each other in pairs, wherein the cranio-caudal pictures of the right and the left breast and the mediolateral-oblique pictures of the right and the left breast are subjected to a comparison of symmetry. This comparison of symmetry between the left and the right breast of a patient plays an essential role for diagnosis, since architectural disturbances in the form of asymmetries between the left and the right breast can be an indication for a tumor possibly present in a breast.

In such mammography examinations, a physician faces the problem that the breasts shown mostly cover only a small part of the mammograms, whereas most of the mammogram is filled by the background region which contains no information. In addition, the mammograms generally are offset against each other and thus must be positioned relative to each other, in order to enable an appropriate comparison of the mammograms.

Exemplary mammograms 2a, 2b, 2c, 2d of a mammography examination are shown in FIG. 1, in which the cranio-caudal (CC) pictures of the right (R) and the left (L) breast and the medio-lateral (MLO) pictures of the right (R) and the left (L) breast are shown one beside the other. In order to optimally position and scale the mammograms 2a, 2b, 2c, 2d for display on the evaluation device, there is first determined one contour line K1, K2, K3, K4 each, which separates the breast shown in the object area 20 from the background region 21 of the mammogram. After the contour line for each mammogram 2a, 2b, 2c, 2d is determined, the image center of gravity M1, M2, M3, M4 is determined for each mammogram 2a, 2b, 2c, 2d and one altitude line H1, H2, H3, H4 each is determined, which extends through the image center of gravity M1, M2, M3, M4. Due to the altitude lines H1, H2, H3, H4, the mammograms 2a, 2b, 2c, 2d each are vertically aligned with each other in pairs for the cranio-caudal (CC) and mediolateral-oblique (MLO) pictures.

Subsequently, a surrounding rectangle R1, R2, R3, R4 is determined using the contour lines K1, K2, K3, K4 for each mammogram 2a, 2b, 2c, 2d, wherein the vertical alignment using the altitude lines H1, H2, H3, H4 is considered when determining the surrounding rectangle R1, R2, R3, R4. From the surrounding rectangles R1, R2, R3, R4, the greatest rectangle is selected, and using this rectangle—in the case shown in FIG. 1 the rectangle R3—an optimum scaling factor is determined, by means of which all mammograms 2a, 2b, 2c, 2d are scaled uniformly. The scaling factor is determined such that the breast enclosed by the greatest rectangle R3 optimially fills the corresponding mammogram 2c by minimizing the background region 21. A uniform scaling factor is used here in all directions, so that the aspect ratio of each of the mammograms 2a, 2b, 2c, 2d is not changed. In the case shown in FIG. 1, the scaling factor is chosen such that the breast shown in the mammogram 2c is maximally enlarged in horizontal direction and thus extends over the entire display region, corresponding to the region S3. The mammograms 2a, 2b, 2c, 2d then are output exclusively in the regions S1, S2, S3, S4 as shown in FIG. 1.

An essential advantage of the automatic positioning and scaling of the mammograms 2a, 2b, 2c, 2d in a mammography examination consists in that a manual adjustment of the mammograms 2a, 2b, 2c, 2d by a user no longer is required, so that diagnosis and evaluation of the mammograms 2a, 2b, 2c, 2d is considerably facilitated for the physician. Positioning is effected completely automatically by the evaluation device, without an interaction by the user being necessary.

The evaluation device enables a physician to directly enter findings into a mammogram 2a, 2b, 2c, 2d to be examined. For this purpose, it is required that the contour lines K1, K2, K3, K4 enclosing the object area 20 of each mammogram 2a, 2b, 2c, 2d are reliably detected, as is for instance subject-matter of DE 10 2006 021 042 A1 and will subsequently not be explained in detail.

Figure 2:
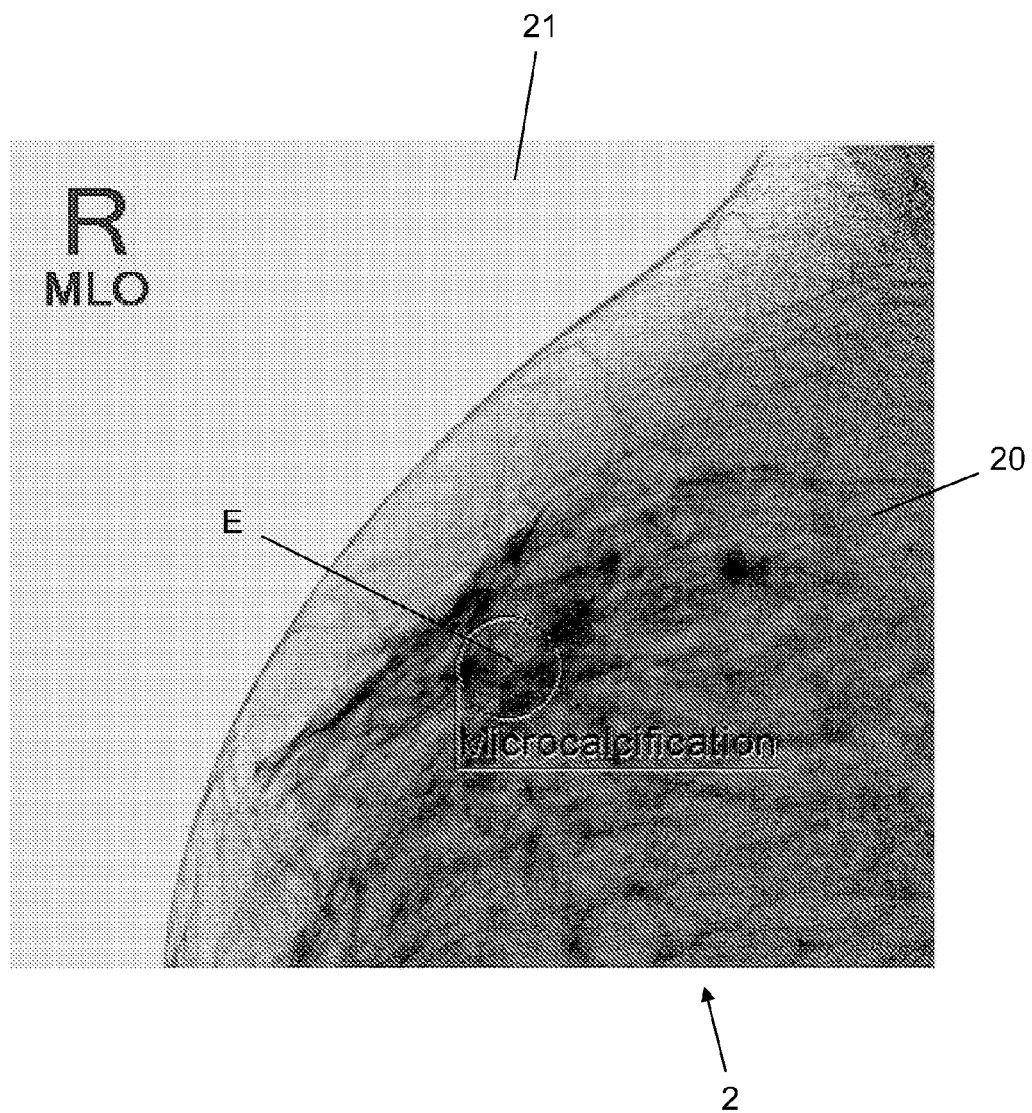
FIG. 2 shows a section of a mammogram with findings entered.

The method for processing findings directly entered in a digital mammogram will now be explained in detail with reference to FIG. 2 to 5. In the examination of one or more mammograms created in an examination, a physician directly enters findings E into a mammogram 2, as shown in FIG. 2, wherein a selection box with predefined findings entries (for instance the possible entries "microcalcification", "densification focus", "asymmetry" or the like) can be provided. For transferring the findings entered into a standardized findings input mask EM (see FIG. 3A), the contour line of the breast shown in the mammogram 2 is determined from the mammogram 2. By imaging the contour line onto the findings input mask EM, which in a standardized way indicates the standard shape of the object to be evaluated, the coordinates of the findings E entered are transferred into the findings input mask EM. In the findings input mask EM, the location of the findings E is determined by imaging the breast described by the contour line onto the standardized findings input mask EM. In this way, the findings E are transferred into the findings input mask EM and displayed in the findings input mask EM. The standardized findings input mask EM can indicate for instance the standard contour of an average left and right breast in a cranio-caudal and mediolateral-oblique view and serves the physician for visualizing and illustrating the findings E.

Figure 3A:
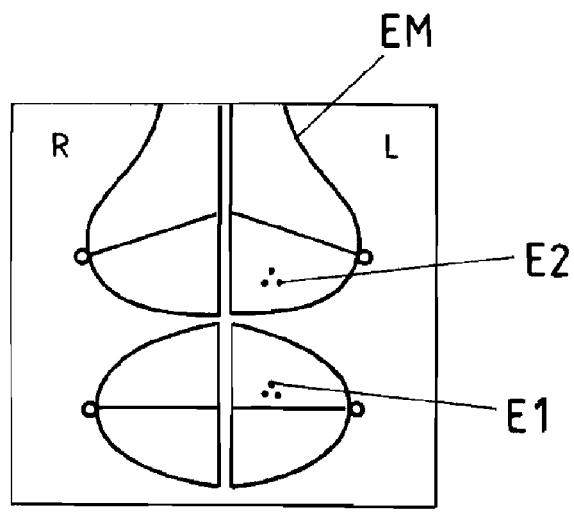
FIG. 3A shows a view of a standardized findings input mask for representing findings entered.
Figure 3B:
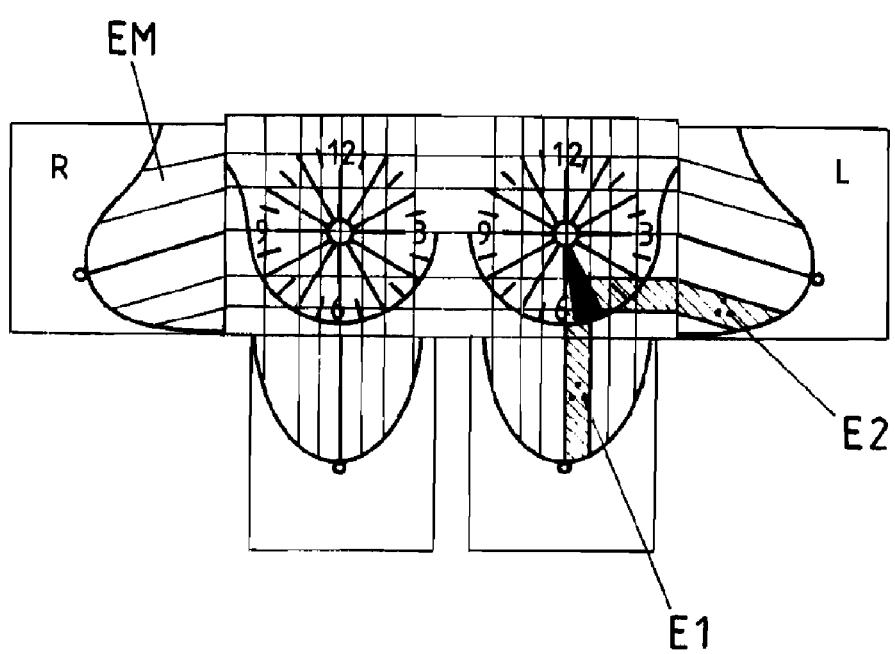
FIG. 3B shows a schematic representation of a clock time model for representing findings entered.

As shown in FIGS. 3A and 3B, two findings E1, E2 must be entered in the different mammograms for localizing a focus of suspicion, of which the findings E1 are entered in the cranio-caudal view and the other findings E2 are entered in the mediolateral-oblique view of the corresponding breast. The findings E2 in the mediolateral-oblique mammogram (e.g. mammogram 2d of the left breast, see FIG. 1) are automatically transferred into a mediolateral-oblique view of the findings input mask EM (see upper half of the image in FIG. 3A), whereas the findings E1 in the cranio-caudal mammogram (e.g. mammogram 2b of the left breast, see FIG. 1) are displayed correspondingly in a cranio-caudal view of the findings input mask EM.

The findings E1, E2 entered are automatically documented in a so-called clock time model, in which, similar to aviation, the location of the findings is displayed by a clock time in the findings input mask EM. The clock time here indicates a direction proceeding from a central point of the breast, in which the findings E1, E2 entered can be found in the breast. The clock time model employs a clock whose center corresponds to the nipple in a front view of the breast and in which a focus of suspicion corresponding to the findings E1, E2 is localized in its direction proceeding from the nipple by indicating a clock time. The clock time should be interpreted in the front view of the breast: 12 o'clock corresponds to a central position above the nipple; 3 o'clock corresponds to a position to the right at the level of the nipple, etc.

The information as to whether the focus of suspicion is located to the right or to the left of the nipple is taken from the cranio-caudal views (mammograms 2a, 2b), whereas the mediolateral-oblique views (mammograms 2c, 2d) provide the information as to whether a focus of suspicion is located above or below the nipple. The coordinates of the findings E1, E2 are converted into the clock time model and displayed, as is graphically illustrated in FIG. 3B. In the example shown in FIG. 3B, the findings E1, E2 entered by the physician thus are automatically converted into the display "microcalcification at 5.30 a.m." and subsequently stored as structured text report.

The transfer of the findings E1, E2 entered in the mammogram 2, 2a, 2b, 2c, 2d into the findings input mask EM as shown in FIG. 3A and the transformation into the clock time model as shown in FIG. 3B does not lead to any problems, as long as the findings E1, E2 entered are localized sufficiently far away from the level of the nipple of the breast. However, if findings E1, E2 are located at the level of the breast in the mediolateral-oblique view and/or the cranio-caudal view, transferring the findings E1, E2 into the clock time model can lead to discontinuities and therefore an inaccurate display and storage in the clock time model. This is due to the fact that depending on whether findings are located just to the right or left or just above or below the nipple, the clock time model possibly is discontinuous. For instance, if the findings E2 shown in FIG. 3A and 3B were located approximately at the level of the nipple, the clock time indicated in the clock time model would jump to about 6 o'clock or about 12 o'clock, depending on whether the findings E2 are located just above or just below the nipple. This is disadvantageous and should be avoided, as in a future treatment an attending physician will possibly look for a focus of suspicion at a wrong point.

To avoid such jumps, an embodiment of the method presented here provides to divide the object area 20 of the mammogram 2a, 2b, 2c, 2d into two partial areas, which then are each imaged onto an allocated mask region of the findings input mask EM. Due to the unambiguous allocation of findings E, E1, E2 entered to one of the partial areas, it is determined and defined unambiguously as to whether the findings E, E1, E2 entered are located above or below or to the right or left of the nipple, so that discontinuities and jumps in the clock time model are avoided.

Figure 5A:
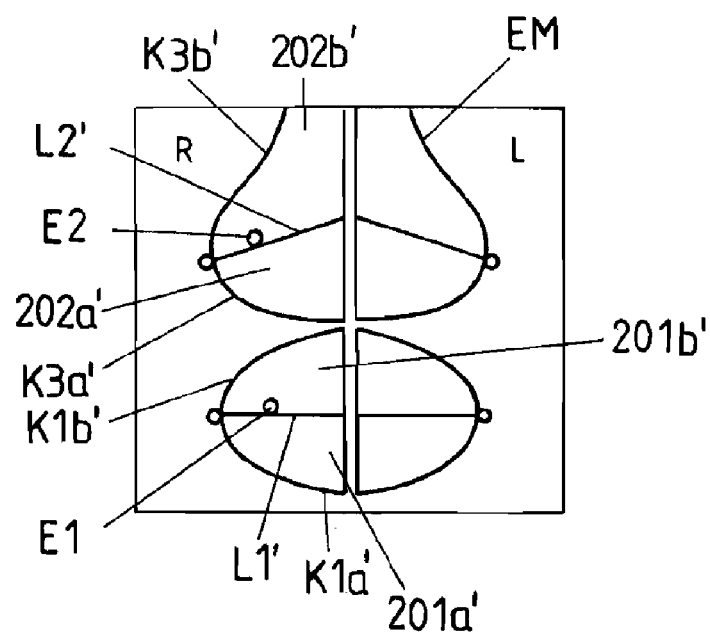
FIG. 5A shows a representation of the findings transferred into the findings input mask as shown in FIG. 4.

The corresponding procedure will be explained in detail below with reference to FIG. 4 and FIG. 5A, 5B.

FIG. 4 first of all shows the views of the mammograms 2a, 2b, 2c, 2d of FIG. 1, wherein one nipple line L1, L2 each is indicated in the views 2a, 2c to be evaluated. The nipple line L1, L2 each extends between the nipple Ma1, Ma2 of the breast and a starting point P1, P2 of the altitude lines H1, H3 extending through the image centers of gravity M1, M3. The position of the nipple Ma1, Ma2 has been determined automatically with reference to the contour lines K1, K3 of the mammograms 2a, 2c; it can, however, subsequently be corrected interactively by a user—the evaluating physician. The nipple line L1, L2 is displayed while making the evaluation, so that while making the evaluation, the user already obtains the information as to whether findings E1, E2 entered are located above or below the nipple line L1, L2, and accordingly the user can check the correct transfer into the clock time model.

The user enters the findings E1, E2 into the mammogram 2a, 2c, wherein a complete findings input requires a localization in the cranio-caudal view and mediolateral-oblique view of the breast to be evaluated—in this case the right-hand breast (see mammograms 2a, 2c in FIG. 4). Findings input is effected as explained above with reference to FIG. 2. The evaluation device automatically transfers the findings E1, E2 entered into the findings input mask EM (see FIG. 5A) by dividing the object area 20 of each mammogram 2a, 2c into two partial areas 201a, 201b and 202a, 202b, respectively, which are separated from each other by the nipple line L1, L2 and which each are separately imaged onto the input mask EM.

The partial areas 201a, 201b and 202a, 202b, respectively, each are defined section by section by a partial contour K1a, K1b and K3a, K3b, respectively, which corresponds to a section of the contour line K1, K3 of the object area 20, and the nipple line L1, L2. For transferring the findings E1, E2 into the findings input mask EM, the partial areas 201a, 201b, 202a, 202b each are imaged onto a corresponding mask region 201a', 201b', 202a', 202b' of the findings input mask EM, wherein the partial contours K1a, K1b, K3a, K3b are imaged onto partial contours K1a', K1b', K3a', K3b' of the findings input mask EM and the nipple line L1, L2 is imaged onto an allocated nipple line L1', L2'.

For imaging the partial areas 201a, 201b, 202a, 202b, a square or linear deformation can for instance be used, in which the partial areas 201a, 201b, 202a, 202b are deformed such that the partial contours K1a, K1b, K3a, K3b come to lie on the allocated deformed partial contours K1a', K1b', K3a', K3b' of the input mask EM. The findings E1, E2 entered are unambiguously allocated to one partial area each (here the partial areas 201b (findings E1), 202b (findings E2)) and are correspondingly transferred into the input mask EM by maintaining the allocation (see FIG. 5A). It is decisive here that in the input mask EM the findings E1, E2 entered, which in the mammograms 2a, 2c are located above the nipple line L1, L2, also are located above the allocated nipple line L1', L2', and due to the allocation to the partial areas 201b, 202b and 201b', 202b', respectively, it thus is determined unambiguously whether the findings E1, E2 are located above or below the nipple line L1, L2 and L1', L2', respectively.

Figure 5B:
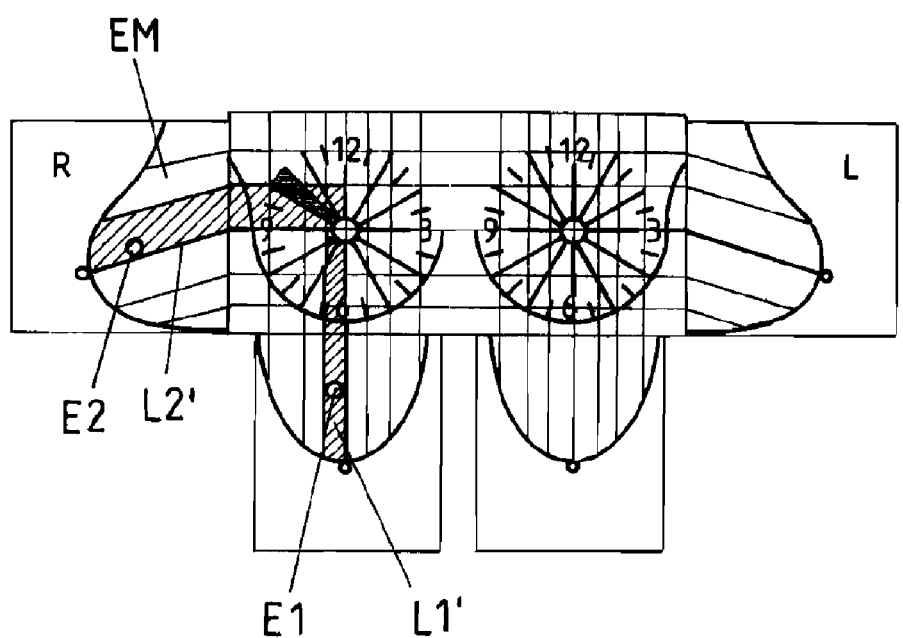
FIG. 5B shows a representation of the findings transformed into the clock time model as shown in FIG. 4.

With reference to the findings E1, E2, which indicate the same focus of suspicion in different views, namely the cranio-caudal view of mammogram 2a and the mediolateral-oblique view of mammogram 2c, the transformation into the clock time model now is effected, as shown in FIG. 5B. In the example illustrated in FIG. 5A and 5B, the focus of suspicion E1 in the cranio-caudal view corresponding to mammogram 2a is located just to the left of the nipple line L1' in the findings input mask EM, and the focus of suspicion E2 in the mediolateral-oblique view corresponding to mammogram 2c is located just above the nipple line L2' of the findings input mask EM, so that the transformation into the clock time model of the left-hand breast provides a focus of suspicion at 10.30 a.m. with reference to the nipple. Using this information, the findings are stored and in the subsequent treatment, these findings assist an attending physician in localizing the focus of suspicion.

The ideas underlying the invention are not restricted to the embodiments described above. In particular, it is conceivable, for instance, to choose another division of the partial areas, in which for instance the nipple line does not extend linearly or has other starting points. It is essential here that the object area of a mammogram is not treated uniformly, but is divided into partial areas, which then are processed separate from each other—but with a continuous connection.

The invention claimed is:

1. A method for processing findings entered in a mammogram, the method comprising:
   displaying a digital mammogram via an evaluation device;
   entering, by means of an input device, findings directly into the mammogram displayed via the evaluation device;
   automatically transferring the findings from the mammogram into a findings input mask;
   wherein transferring the findings from the mammogram into the findings input mask comprise determining a contour line of an object area surrounding an object in the mammogram,
   dividing the object area of the mammogram into two partial areas;
   imaging each object area onto an allocated mask region of the findings input mask;
   allocating the entered findings to one of the partial areas; and transferring the entered findings into the findings input mask with reference to the allocated partial area.

2. The method of claim 1, wherein the object area is divided into the partial areas by a nipple line, which extends through the nipple of a breast represented in the mammogram.

3. The method of claim 2, wherein the nipple line extends through the nipple and a starting point of an altitude line extending horizontally through the image center of gravity of the mammogram.

4. The method of claim 2, wherein the position of the nipple of a breast represented in a mammogram is determined automatically.

5. The method of claim 2, further comprising:
displaying the nipple line in the mammogram during input of the findings.

6. The method of claim 5, wherein the nipple line is adjustable interactively.

7. The method of claim 1, wherein the partial areas section by section are defined by one partial contour each, which corresponds to a section of the contour of the object area and is imaged onto a partial contour of the findings input mask.

8. The method of claim 1, wherein the partial areas of the object area of the mammogram are imaged onto the mask regions of the findings input mask using a square or linear deformation.

9. The method of claim 1, further comprising:
transforming coordinates of the findings into a clock time model; and
outputting coordinates of the findings using the clock time model.

* * * * *